(12) United States Patent
Habegger et al.

(10) Patent No.: US 10,835,382 B2
(45) Date of Patent: Nov. 17, 2020

(54) TIBIAL TRAY WITH REMOVABLE SPIKES

(71) Applicant: Zimmer, Inc., Warsaw, IN (US)

(72) Inventors: Abraham P. Habegger, Warsaw, IN (US); Steven Lyons, Warsaw, IN (US); Wolfgang Klauser, Warsaw, IN (US); Vanessa Croll, Warsaw, IN (US); Michael John Collins, Swindon (GB)

(73) Assignee: Zimmer, Inc., Warsaw, IN (US)

( * ) Notice: Subject to any disclaimer, the term of this patent is extended or adjusted under 35 U.S.C. 154(b) by 45 days.

(21) Appl. No.: 15/874,147

(22) Filed: Jan. 18, 2018

(65) Prior Publication Data

US 2018/0206996 A1 Jul. 26, 2018

Related U.S. Application Data

(60) Provisional application No. 62/448,492, filed on Jan. 20, 2017.

(51) Int. Cl.
*A61F 2/38* (2006.01)
*A61F 2/30* (2006.01)
*A61B 17/17* (2006.01)

(52) U.S. Cl.
CPC .......... *A61F 2/389* (2013.01); *A61F 2/30734* (2013.01); *A61F 2/3859* (2013.01); *A61B 17/1764* (2013.01); *A61F 2/30767* (2013.01); *A61F 2002/30535* (2013.01); *A61F 2002/30604* (2013.01); *A61F 2002/30841* (2013.01); *A61F 2002/30878* (2013.01)

(58) Field of Classification Search
CPC ............................................ A61F 2002/30736
See application file for complete search history.

(56) References Cited

U.S. PATENT DOCUMENTS

| 5,019,103 | A | * | 5/1991 | Van Zile | ............. | A61F 2/30734 623/20.34 |
| 5,609,641 | A | | 3/1997 | Johnson et al. | | |
| 5,683,469 | A | | 11/1997 | Johnson et al. | | |
| 5,911,758 | A | * | 6/1999 | Oehy | ...................... | A61F 2/389 623/20.32 |

(Continued)

FOREIGN PATENT DOCUMENTS

WO 2018136593 A1 7/2018

OTHER PUBLICATIONS

"International Application Serial No. PCT US2018 014151, International Search Report dated Jul. 5, 2018", 6 pgs.

(Continued)

*Primary Examiner* — Megan Y Wolf
(74) *Attorney, Agent, or Firm* — Schwegman Lundberg & Woessner, P.A.

(57) ABSTRACT

According to one example, a tibial replacement assembly for a knee arthroplasty can be configured to couple to a resected proximal surface of a tibia of a human knee. The tibial replacement assembly can include a tibial tray and a first spike. The tibial tray can include a proximal surface and a distal surface opposing the proximal surface. The distal surface can be configured to be disposed on a resected proximal surface of a tibia. The first spike can be removably secured to the tibial tray and can extend generally distally away from the distal surface. The first spike can be configured to extend beneath the resected proximal surface of the tibia.

15 Claims, 6 Drawing Sheets

(56) References Cited

U.S. PATENT DOCUMENTS

| | | |
|---|---|---|
| 2004/0034432 A1 | 2/2004 | Hughes et al. |
| 2008/0015691 A1* | 1/2008 | Wyss .................... A61F 2/3603 623/16.11 |
| 2008/0133020 A1 | 6/2008 | Blackwell et al. |
| 2009/0062926 A1 | 3/2009 | Wyss |
| 2009/0265011 A1 | 10/2009 | Mandell |
| 2010/0222890 A1 | 9/2010 | Barnett et al. |
| 2014/0277539 A1* | 9/2014 | Cook ................ A61F 2/30734 623/20.32 |

OTHER PUBLICATIONS

"International Application Serial No. PCT US2018 014151, Written Opinion dated Jul. 5, 2018", 6 pgs.

* cited by examiner

TIBIAL TRAY WITH REMOVABLE SPIKES

CLAIM OF PRIORITY

This application claims the benefit of priority to U.S. Provisional Application Ser. No. 62/448,492, filed on Jan. 20, 2017, which is incorporated herein by reference in its entirety.

FIELD

The present subject matter relates to orthopedic prostheses and, more particularly, to prostheses, systems and methods used in knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial bearing component and a tibial component implanted on the proximal end of a tibia to replicate the function of a healthy natural knee. Various types of arthroplasties are known including a total knee arthroplasty, where all of the articulating compartments of the joint are repaired with prosthetic components.

OVERVIEW

This disclosure pertains generally to tibial prostheses, systems, and methods for a knee arthroplasty and/or as part of a knee revision surgery. The present inventors have recognized, among other things, that a patient may possess bone deficits or undesirable bone on all or some of the patient's tibia. Accordingly, portions of the tibia may be insufficient for mounting a tibial prosthesis. In such cases, the patient's tibia may require deeper resection and may additionally require augments to connect to a resected tibial and the tibial tray to place the tibial tray in alignment with femoral condyles or artificial condyles. Whether the augments or tibial tray is to connect to the resected tibia, it is generally desirable to firmly secure the tibial prosthesis to the tibia. In some cases, spikes are used to aid securing the tibial prosthesis to the tibia, as removable and exchangeable spikes can provide additional surface area for the bone to engage and can provide additional transmission of forces to and from the tibia in different areas of the tibia where there may be more desirable bone for mounting. In prior cases, tibial prostheses having spikes include a tibial tray with integral spikes have been used. However with this solution, augments are placed on or over the spikes, effectively shortening a tibial penetrating depth of the spikes. In other cases, long spikes may be used to extend an optimal depth past the augments into the tibia. In these cases, the spikes used may be much longer than is necessary to engage the bone when no augments are used. Thus, dedicated tibial tray designs with integral spikes having various lengths of spikes were manufactured leading to high inventory. Some tibial tray designs with spikes of a certain length were never utilized. Thus, the present inventors propose a tibial tray and augment system that includes spikes configured to removably and interchangeably couple to either one or both of the tibial tray and the augments.

To further illustrate the apparatuses and systems disclosed herein, the following non-limiting examples are provided:

In Example 1, a tibial replacement assembly for a knee arthroplasty, the tibial replacement assembly configured to couple to a resected proximal surface of a tibia of a human knee, can include subject matter (such as a device or apparatus) tibial replacement assembly comprising: a tibial tray comprising a proximal surface and a distal surface opposing the proximal surface, the distal surface configured to be disposed on a resected proximal surface of a tibia; and a first spike removably secured to the tibial tray and extending generally distally away from the distal surface, the first spike configured to extend beneath the resected proximal surface of the tibia.

In Example 2, the tibial replacement assembly of Example 1 can optionally be configured such that the tibial tray further comprises: a first bore extending from the distal surface into the tibial tray.

In Example 3, the tibial replacement assembly of any one or any combination of Examples 1-2 can optionally be configured such that the first spike is removably received in and securable to the first bore.

In Example 4, the tibial replacement assembly of any one or any combination of Examples 1-3 can optionally be configured to further comprise: a first augment having a second bore therein, the augment configured to abut the distal surface of the tibial tray to align the second bore with the first bore.

In Example 5, the tibial replacement assembly of any one or any combination of Examples 1-4 can optionally be configured such that the first spike is removably securable to the second bore of the augment and the first bore of the tibial tray.

In Example 6, the tibial replacement assembly of any one or any combination of Examples 1-5 can optionally be configured to further comprise: a keel extending generally distally away from the distal surface of the tibial tray; and a second augment configured to abut a lateral side of the tibial tray, wherein the first augment is configured to abut a medial side of the tibial tray, and wherein the first and second augments are disposed around the keel.

In Example 7, the tibial replacement assembly of any one or any combination of Examples 1-6 can optionally be configured such that the tibial tray further comprises a plurality of bores including the first bore, each of the plurality of bores extending from the distal surface into the tibial tray.

In Example 8, the tibial replacement assembly of any one or any combination of Examples 1-7 can optionally be configured to further comprise: a plurality of a spikes including the first spike, each of the plurality of spikes configured to secure to any of the plurality of the bores.

In Example 9, the tibial replacement assembly of any one or any combination of Examples 1-8 can optionally be configured such that the plurality of spikes includes a quantity of spikes that is lower than a quantity of the plurality of bores, and wherein the plurality of spikes are each configured to secure into any of the plurality of bores in a pattern as desired.

In example 10, a tibial replacement system for a revision knee arthroplasty, the tibial replacement system couplable to a resected proximal surface of a tibia of a human knee, can include subject matter (system), the tibial replacement system comprising: a tibial tray comprising a proximal surface and a distal surface opposing the proximal surface; and an augment comprising: an augment proximal surface configured to couple to the distal surface of the tibial tray; an augment distal surface opposite the augment proximal surface, wherein at least one or both of the distal surface of the tibial tray and the augment distal surface are configured to be disposed on the resected proximal surface of the tibia; and a first spike removably securable to one or both of the augment and the tibial tray, the first spike extending generally distally away from the augment distal surface, the first spike configured to extend beneath the resected proximal surface of the tibia.

In Example 11, the tibial replacement system of Example 10 can optionally be configured such that the tibial tray further comprises: a first bore extending from the distal surface into the tibial tray; and wherein the augment further comprises a first augment having a second bore therein, wherein the first augment is configured to abut the distal surface of the tibial tray to align the second bore with the first bore.

In Example 12, the tibial replacement system of any one or any combination of Examples 10-11 can optionally be configured to further comprise: a keel extending generally distally away from the distal surface of the tibial tray; and wherein the augment further comprises a second augment configured to abut a lateral side of the tibial tray, wherein the first augment is configured to abut a medial side of the tibial tray, and wherein the first and second augments are disposed around the keel.

In Example 13, the tibial replacement system of any one or any combination of Examples 10-12 can optionally be configured such that the tibial tray further comprises: a plurality of bores including the first bore, each extending from the distal surface into the tibial tray; and a plurality of spikes including the first spike, each spike configured to secure to any of the plurality of the bores.

In Example 14, the tibial replacement system of any one or any combination of Examples 10-13 can optionally be configured such that the plurality of spikes includes a quantity of spikes that is lower than a quantity of the plurality of bores, and wherein the plurality of spikes are each configured to secure into any of the plurality of bores in a pattern as desired.

In Example 15, the tibial replacement system of any one or any combination of Examples 10-14 can optionally be configured such that the augment includes a second plurality of bores, and wherein the plurality of spikes are each configured to secure into any of the plurality of bores and any of the second plurality of bores.

In example 16, a tibial replacement system for a revision knee arthroplasty, the tibial replacement system couplable to a resected proximal surface of a tibia of a human knee, can include subject matter (such as a system), the tibial replacement system comprising: a tibial tray comprising a proximal surface and a distal surface opposing the proximal surface; and an augment comprising: an augment proximal surface couplable to the distal surface of the tibial tray; and an augment distal surface opposite the augment proximal surface, wherein the distal surface of the tibial tray and the augment distal surface are both configured to be disposed on a resected proximal surface of a tibia; and a plurality of spikes configured to be removably secured to one or more of the augment and the tibial tray, each of the plurality of spikes configured to extend past the augment distal surface to beneath the resected proximal surface of the tibia.

In Example 17, the tibial replacement system of Example 16 can optionally be configured such that the tibial tray further comprises: a first bore extending from the distal surface into the tibial tray; and wherein the augment further comprises a first augment having a second bore therein, the first augment configured to abut the distal surface of the tibial tray to align the second bore with the first bore.

In Example 18, the tibial replacement system of any one or any combination of Examples 16-17 can optionally be configured to further comprise: a keel extending generally distally away from the distal surface of the tibial tray; wherein the augment further comprises a second augment configured to abut a lateral side of the tibial tray, wherein the first augment is configured to abut a medial side of the tibial tray, and wherein the first and second augments are disposed around the keel.

In Example 19, the tibial replacement system of any one or any combination of Examples 16-18 can optionally be configured such that the tibial tray further comprises a plurality of bores, including the first bore, each bore extending from the distal surface into the tibial tray, wherein the plurality of spikes includes a quantity of spikes that is lower than a quantity of the plurality of bores, and wherein the plurality of spikes are each configured to secure into any of the plurality of bores in a pattern as desired.

In Example 20, the tibial replacement system of any one or any combination of Examples 16-19 can optionally be configured such that the augment includes a second plurality of bores, including the second bore, and wherein the plurality of spikes are each configured to secure into any of the plurality of bores or the second plurality of bores.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates tibial prostheses, systems, and methods. The systems, for example, can include a tibial bearing component, and a femoral component.

The present application relates to devices and methods for a tibial tray and augment system that can be used in or with a knee prosthesis, such as during a knee arthroplasty and/or as part of a later knee revision surgery. As described herein, a tibial plate can be part of a knee prosthesis and the fixation structure can promote securement and/or stabilization of the tibial baseplate to a patient's proximal tibia. An augment system can include two or more augments configured to attach to a tibial baseplate and can be located between the tibial baseplate and a resected surface of a tibia. The augment system can include plates of variable thickness and plates formed of different materials. The augment system can facilitate restoration of the anatomic joint line and address bone deficits on all or some of a proximal surface of a patient's tibia. In an example, the augment system can be used in combination with an implant structure configured to replace damaged bone within a medullary region of the patient's tibia.

As used herein, the terms "proximal" and "distal" should be given their generally understood anatomical interpretation. The term "proximal" refers to a direction generally toward the torso of a patient, and "distal" refers to the opposite direction of proximal, i.e., away from the torso of a patient. It should be understood that the use of the terms "proximal" and "distal" should be interpreted as though the patient were standing with the knee joint in extension despite the apparatuses described herein generally being used with the knee joint in flexion. The intent is to differentiate the terms "proximal" and "distal" from the terms "anterior" and "posterior". As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior".

Figure 1:
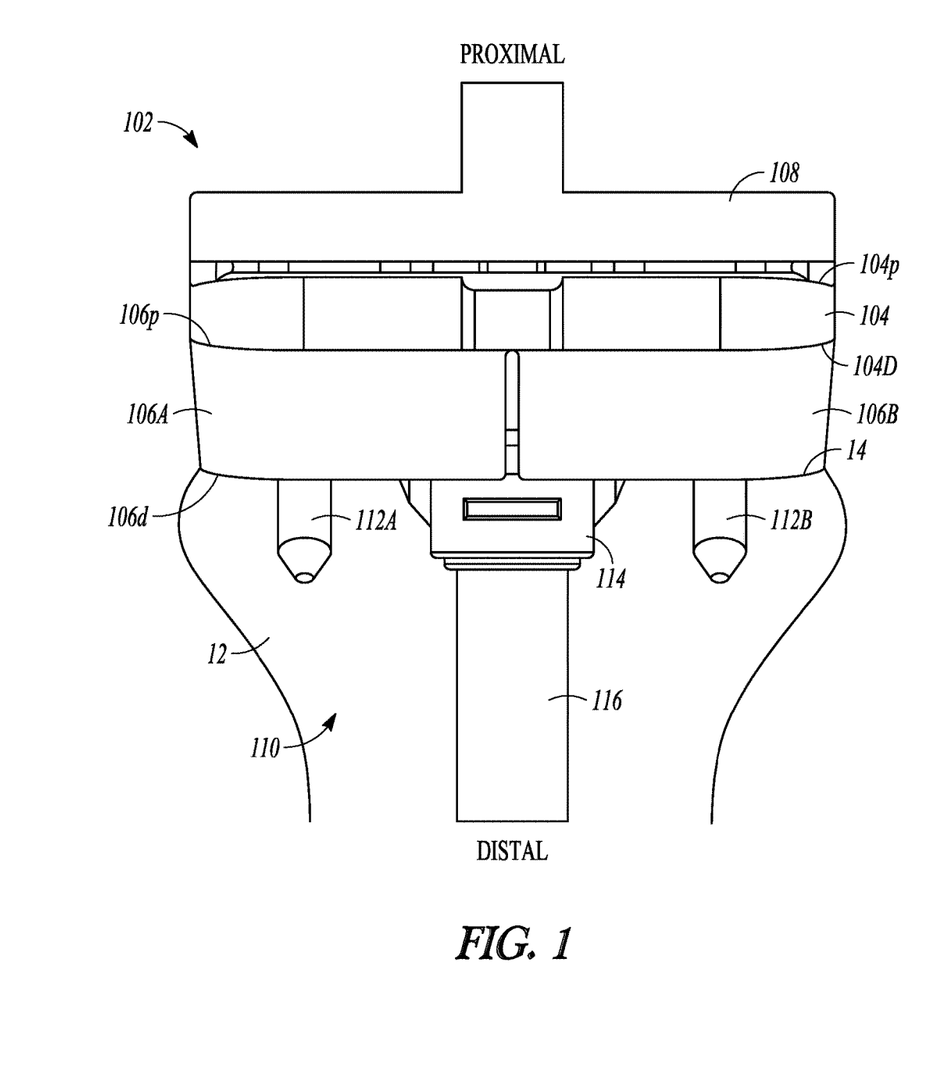
FIG. 1 shows an elevation view of a proximal end of a natural tibia coupled to a tibial replacement system in accordance with an example of the present application.

FIG. 1 illustrates an elevation view of a proximal end of tibial replacement system 102 coupled to tibia 12, in accordance with an example of the present application. Tibia 12 can include resected proximal surface 14 that can be formed from a resection during a knee arthroplasty procedure. If tibial replacement system 102 is used as part of a revision to the patient's knee, resected proximal surface 14 can be a second or subsequent resection to tibia 12 to remove diseased or undesirable bone.

Tibial replacement system 102 can include tibial tray 104, augments 106A and 106B, bearing 108, keel assembly 110, and spikes 112A and 112B. Keel assembly 110 can include a keel stem (not shown in FIG. 1), keel 114, and tibial keel stem 116. Tibial tray 104 can include proximal side 104$p$ and distal side 104$d$. Augments 106A and 106B include proximal side 106$p$ and distal side 106$d$. Also shown are orientation indications Proximal, Distal, Medial, and Lateral.

As part of a knee arthroplasty, tibial replacement system 102 can be configured to interface with and articulate with a femoral replacement implant (not shown), in some examples. In some examples, a distal portion of tibial replacement system 102 can connect to tibia 12, as discussed further below.

In some examples, tibial tray 104 can include proximal side 104$p$, which can be configured to couple to and interface with bearing 108. Tibial tray 104 can also include distal side 104$d$, which can be coupled to augments 106A and 106B according to some examples. According to other examples, distal side 104$d$ can be configured to interface with and rest upon resected proximal surface 14. Proximal side 104$p$ can be opposed to distal side 104$d$. Augments 106A and 106B can also include proximal and distal sides 106$p$ and 106$d$, respectively. Augment 106A can be coupled at proximate side 106$p$ to distal side 104$d$ at a lateral side of tibial tray 104. Similarly, augment 106B can be coupled at proximate side 106$p$ to distal side 104$d$ at a medial side of tibial tray 104. Proximal side 106$p$ can be opposed to distal side 106$d$. Distal sides 106$d$ of augments 106A and 106B can be coupled to tibia 12 at resected proximal surface 14.

Keel assembly 110 can be coupled to distal side 104$d$ of tibial tray 104 in some examples. More specifically, keel 114 can be coupled to a keel stem (not shown) and can extend distally away from distal side 104$d$ of tibial tray into a recess in tibia 12. Tibial keel stem 116 can be coupled to keel 114 or keel stem (not shown) and can also extend distally away from distal side 104$d$ of tibial tray 104 into the recess in tibia 12. For example, the recess can comprise a cavity created along a tibial medullary space of the tibia 12. Keel 114 and tibial keel stem 116 can extend into and engage this tibial medullary cavity of tibia 12, securing tibial replacement system 102 to tibia 12.

Spikes 112A and 112B can comprise attachable and removable features such as fasteners (e.g., nails, pins, screw thread, and the like). According to some examples spikes 112A and 112B can be removably coupled to augments 106A and 106B. According to further examples, spikes 112A and 112B can be removably coupled to tibial tray 104, as described below in FIG. 4. In yet further examples, spikes 112A and 112B can be removably coupled to both the tibial tray 104 and to one or more augments 106A and 106B. Indeed in some examples, spikes 112A and 112B can couple one or more augments 106A and 106B to the tibial tray 104. Spikes 112A and 112B can be secured to augments 106A and 106B and/or tibial tray 104 through a threaded engagement so as to be removable therefrom. According to further examples, spikes 112A and 112B can be attached in a more permanent manner to augments 106A and 106B and/or tibial tray 104 by a press fitting, an adhesive, and the like. Spikes 112A and 112B can extend away from distal sides 106$d$ of augments 106A and 106B, extending through resected proximal surface 14 into tibia 12.

In some surgical procedures, tibia 12 can be resected at resected proximal surface 14, creating an attachment surface for tibial tray 104 to secure to tibia 12. Bearing 108 can then be secured to tibial tray 104 to provide femoral condyles of a femoral implant (not shown) a smooth articulating surface. In some of these examples, spikes 112A and 112B can be secured to tibial tray 104 to engage tibia 12. Then, spikes 112A and 112B can transmit rotational forces between tibia 12 and tibial tray 104.

In some examples, tibia 12 may need to be resected to provide installation and operating clearance for tibial tray 104 and bearing 108 due to the condition of tibia 12. In other examples, tibia 12 may need to be resected to a further depth to provide a solid engagement surface for tibial tray 104 due to the condition of tibia 12 In these other examples, augments 106A and 106B can be secured to resected proximal surface 14 and attached to tibial tray 104, as described above, to make up for absence of bone, and to position bearing 108 and tibial tray 104 in approximately the position of an ideal location of a patient's meniscus and proximal tibia termination. In these examples, spikes 112A and 112B can be secured to augments 106A and 106B to engage tibia 12.

In some examples, spikes 112A and 112B can be configured to transmit kinematic forces created by a patient articulating the knee joint. The forces can be transmitted from augments 106A and 106B to tibia 12 through spikes 112A and 112B, and can be transmitted from tibia 12 to augments 106A and 106B through spikes 112A and 112B. In these examples, augments 106A and 106B can be configured to transmit the forces to and from tibial tray 104.

Because spikes 112A and 112B can be secured to either tibial tray 104 and/or augments 106A and 106B, tibial replacement system 102 provides the benefit of a single system that can be used for procedures having a relatively large variety of tibial resection depths.

Figure 2A:
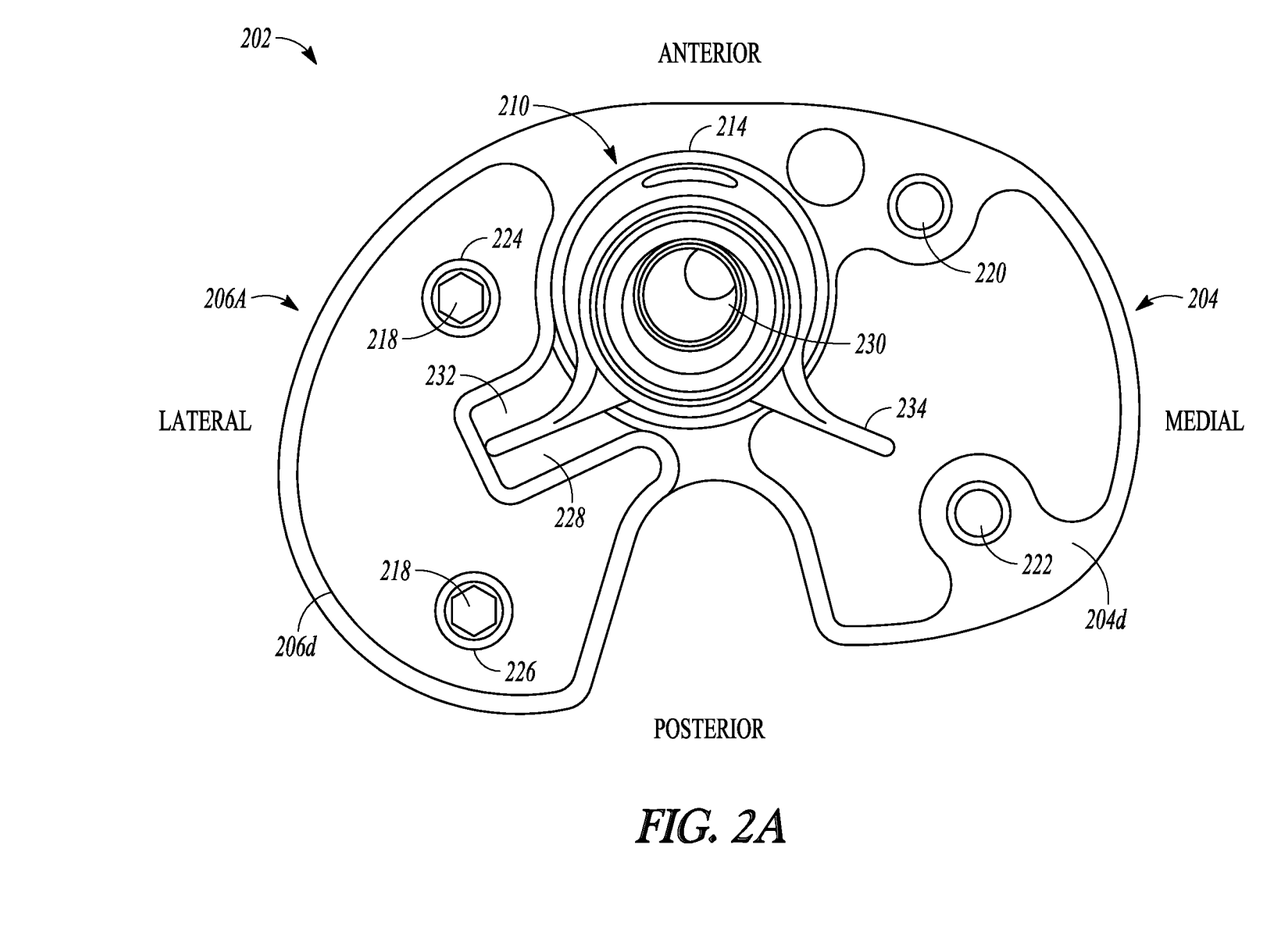
FIG. 2A shows a bottom view of a portion of the tibial replacement system of FIG. 1 in accordance with an example of the present application.
Figure 2B:
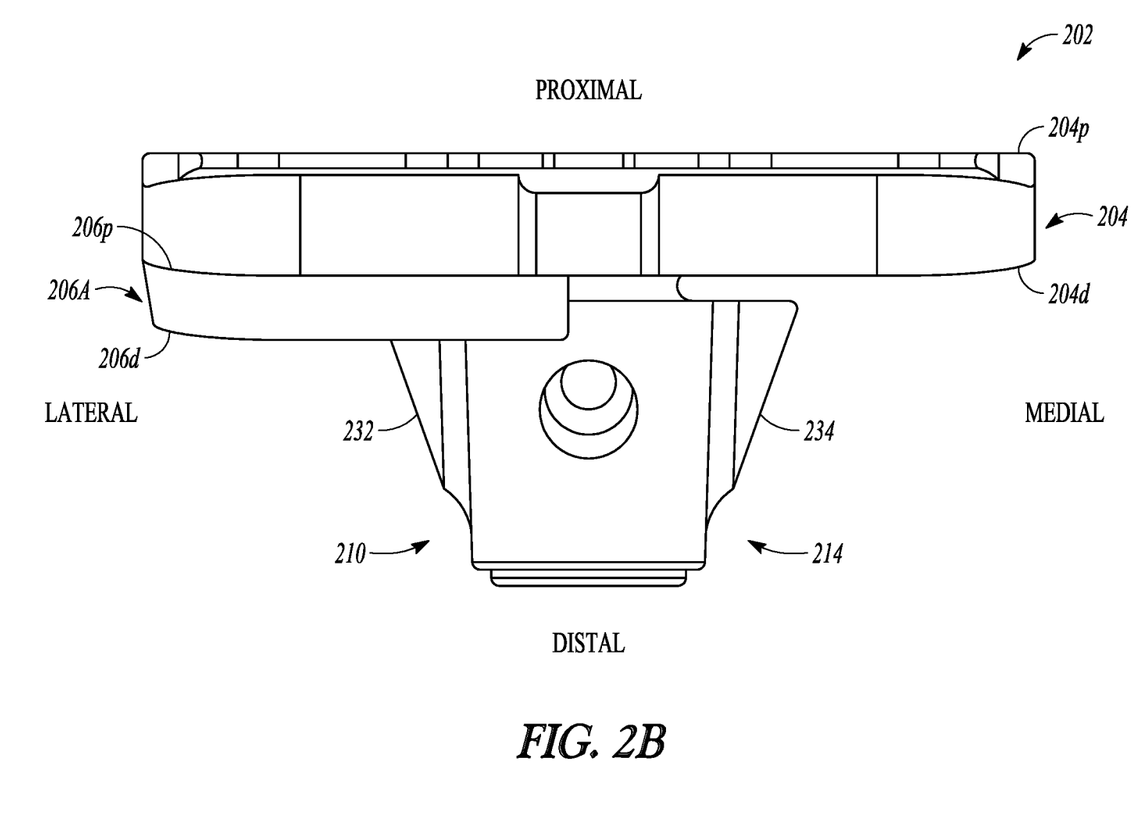
FIG. 2B shows an elevation view of a portion of the tibial replacement system of FIG. 1 in accordance with an example of the present application.

FIG. 2A shows a bottom view of a portion of tibial replacement system 202 and FIG. 2B shows an elevation view of a portion of tibial replacement system 202 in accordance with an example of the present application. FIGS. 2A and 2B are discussed below concurrently and show one of the augments as well as spikes that can be used in tibial replacement system 202 removed.

Tibial replacement system 202 can include tibial tray 204, augment 206A, keel assembly 210, and fasteners 218. Tibial tray 204 can include proximal side 204p and distal side 204d. Tibial tray 204 can also include tray bores 220 and 222. Augment 206A can include proximal side 206p and distal side 206d. Augment 206A can also include augment bores 224 and 226, and recessed portion 228. Keel assembly 210 can include keel 214, and keel stem 230. Keel 214 can include keel fins 232 and 234. Also shown are orientation indications Proximal, Distal, Anterior, Posterior, Medial, and Lateral. The components of tibial replacement system 202 can be connected and operate consistently with tibial replacement system 102 of FIG. 1; however, FIGS. 2A and 2B show additional details of tibial replacement system 202.

Tray bores 220 and 222 can be threaded bores extending from distal side 204d into tibial tray 204 toward proximal side 204p and terminating prior to reaching proximal side 204p. Tray bores 220 and 222 are only shown in FIG. 2A as being on the medial side of tibial tray 204; however, tibial tray 204 can include tray bores that align with augment bores 224 and 226 as well. Spikes, such as spikes 112A and 112B of FIG. 1, can be configured to removably secure to the bores of tibial tray 204 and augment bores 224 and 226. That is, spikes can secure to augment bores 224 and 226 and a portion of the spikes, which can be threaded, can extend through proximal side 206p to engage the bores of tibial tray 204.

Tray bores 220 and 222 can be positioned at various locations about keel assembly 210. In some examples, tray bores 220 and 222 can be positioned toward a periphery of tibial tray 204, as shown in the example of FIG. 2. Similarly, though tibial tray 204 can include four bores (only two tray bores 220 and 222 are shown, with two other tray bores hidden by fasteners 218), tibial tray can include more or less bores, such as 2, 3, 5, 6, 8, 10, and so on. Tray bores 220 and 222 can be threaded to receive fasteners 218 and/or spikes (FIG. 1) as desired.

In some examples, fasteners 218 can be inserts removably fitted (through a threaded engagement or other means), into tray bores 220 and 222. In these examples, spikes can be used to engage the inserts and/or tray bores 220 and 222 to secure augment 206A to tibial tray 204.

In some examples, fasteners 218 may not be used and spikes, such as spikes 112A and 112B of FIG. 1, can be used. In these examples, tray bores 220 and 222 can be threaded to receive spikes, so that the spikes are removably coupled to tibial tray 204 and/or augment 206A, the spikes securing augment 206A to tibial tray 204.

Augment bores 224 and 226 can be threaded bores extending from proximal side 206p into augment 206A toward distal side 206d and extending entirely through augment 206A. Though only augment 206A is shown in FIGS. 2A and 2B, a second augment can also include bores.

In operation of one example, spikes (not shown in FIG. 2A or 2B) can be threaded into any one or both of tray bores 220 and 222 and augment bores 224 and 226.

Fasteners 218 and/or spikes can be used to affix augment 206A to tibial tray 204. In the example shown in FIGS. 2A and 2B, fasteners 218 can be hex head screws, but can be other types of screw, nails, or pins in other examples. In some examples, fasteners 218 can be an adhesive, such as bone cement. Fasteners 218 can be threaded through augment bores 224 and 226 into tray bores (not shown) to secure augment 206A to tibial tray 204. Augment bores 224 and 226 can have a second bore having a smaller diameter on proximal side 206p that allows the shank of fasteners 218 and/or spikes to pass through augment bores 224 and 226, but does not allow the head of fasteners 218 to pass through augment bores 224 and 226. This allows fasteners 218 and/or spikes to apply a force on augment 206A as fasteners 218 are threaded into the bores of tibial tray 204, so that fasteners 218 and/or spikes can secure augment 206A to tibial tray 204.

Recessed portion 228 of augment 206A can define a portion of the periphery of augment 206A near the center of tibial tray 204. Recessed portion 228 can be configured to provide clearance for keel 214, and especially fin 232, allowing keel 214 to pass through augment 206A without making contact.

Keel stem 230 and can extend distally away from the center of distal side 204d of tibial tray 204. Keel 214 can be configured to secure to keel stem 230 and can extend distally away from the center of distal side 204d of tibial tray 204 below resected proximal surface 14 to engage tibia 12 (of FIG. 1). Keel fins 232 and 234 can be projections extending generally radially outward from keel 214. Keel fins 232 and 234 can taper radially inward as they extend distally, as shown in FIG. 2B. Though only two of keel fins 232 and 234 are shown, keel assembly 210 can include more or less fins, such as 0, 1, 3, 4, 5, 6, and so on.

Figure 3:
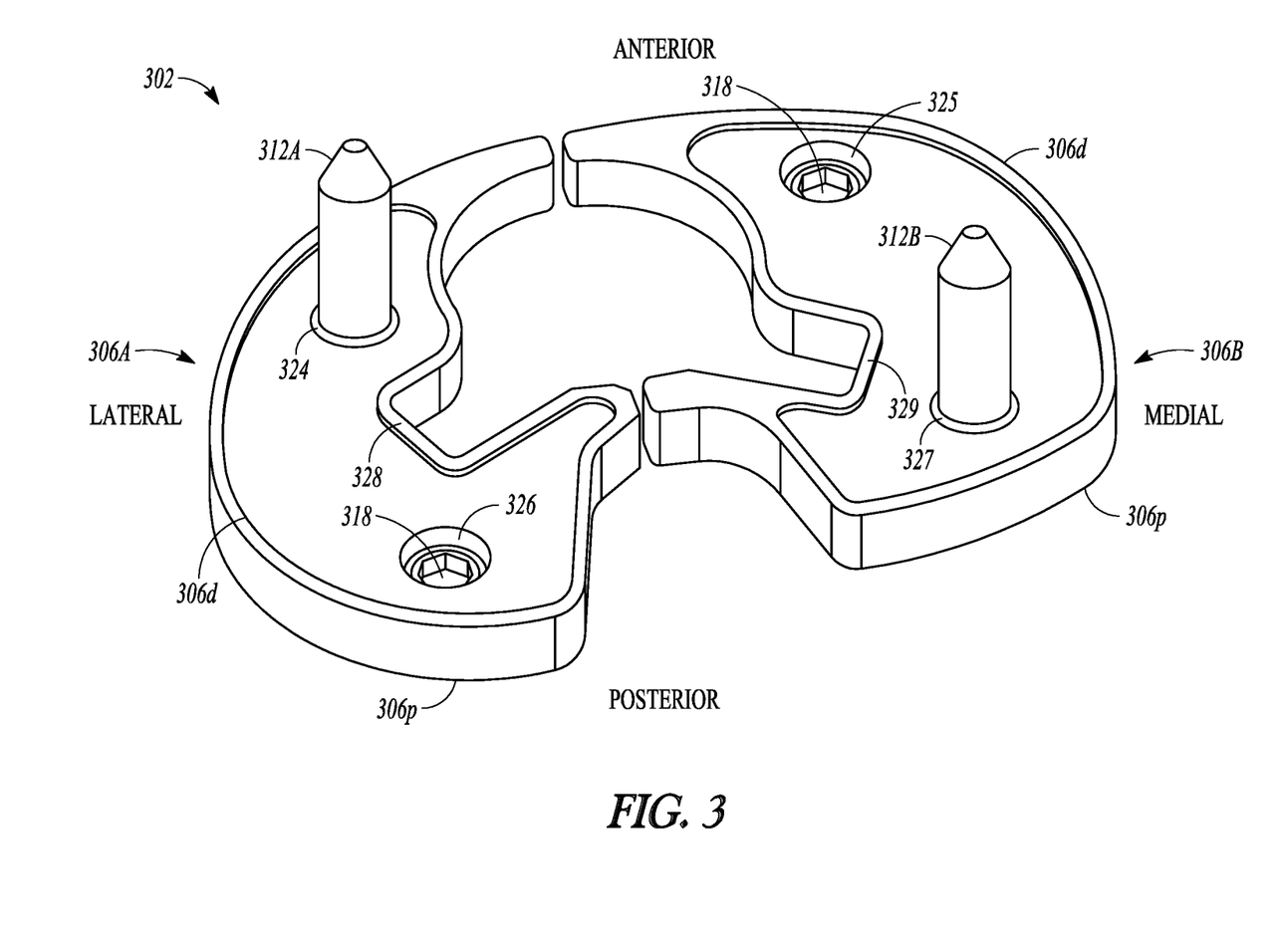
FIG. 3 shows an isometric view of an augment of a tibial replacement system in accordance with an example of the present application.

FIG. 3 shows an isometric view of augments 306A and 306B of a tibial replacement system 302 in accordance with an example of the present application. Augment 306A can include proximal side 306p, distal side 306d, spike 312A, fastener 318, augment bores 324 and 326, and recessed portion 328. Augment 306B can include proximal side 306p, distal side 306d, spike 312B, fastener 318, augment bores 325 and 327, and recessed portion 329. Also shown are orientation indications Anterior, Posterior, Medial, and Lateral. The components of tibial replacement system 302 can be connected and operate consistently with tibial replacement systems 102 and 202 of FIGS. 1, 2A, and 2B; however, FIG. 3 show additional details of augments 306A and 306B.

Augment 306B can include recessed portion 329, which can provide clearance for a keel, such as keel 114 of FIG. 1. Augment 306B can also include augment bores 325 and 327, which can be configured to receive fasteners 318 and spikes, such as spike 312B, as shown in FIG. 3. Augment bores 325 and 327 can include a threaded portion that can be sized to allow fasteners 318 partially pass through bores 325 and 327 without contacting the threaded portion. Once fasteners 318 are secured, the threaded portion can then allow receipt of a threaded portion of a spike, such as spike 312B, as shown in FIG. 3. In some examples, a threaded portion of a spike, such as spike 312, can extend through augment 306B past proximal side 306p to engage a threaded bore of a tibial tray, such as tibial tray 204 of FIG. 2. In these examples, the spike can secure to augment 306B and/or tibial the tibial tray, such as tibial tray 204. Augment bores 324 and 326 of augment 306A can be similarly configured. In some examples, fasteners 318 can be sized so that spikes 312A and 312B contact fasteners 318, in some examples preventing overrotation of spikes 312A and 312B into augment bores 324-327.

Though spike 312B is shown coupled to augment bore 327 in the example of FIG. 3, spike 312B can also be secured to augment bore 325 in other examples. Similarly, though spike 312A is shown as being coupled to augment bore 324 in the example of FIG. 3, spike 312A can also be secured to augment bore 326 in other examples. In some example configurations, spikes 312A and 312B can be secured to augment bores 324 and 325. In some examples, spikes 312A and 312B can be configured to secure of any of augment bores 324, 325, 326, and 327. In some examples, there can be four of augment bores, such as augment bores 324, 325, 326, and 327, and two of spikes, such as spikes 312A and 312B. In other examples, there can be one, three, or four spikes and four bores. In still other examples, there can be many bores, such as 5, 6, 7, or 8 bores for use with 0, 1, 2, 3, 4, 5, 6, 7, or 8 spikes.

In operation of some examples, spikes 312A and 312B can transmit forces from tibia 12 (of FIG. 1) to the tibial tray (such as tibial tray 104 of FIG. 1) and from the tibial tray to tibia 12 by way of augments 306A and 306B. This transmission of forces helps to prevent rotation of augments 306A and 306B (and the tibial tray to which augments 306A and 306B can be secured) relative to tibia 12. By helping to prevent relative rotation of these components, spikes 312A and 312B help to increase the effectiveness and longevity of tibial replacement system 302.

In some examples, portions of resected tibial surface 14 and/or tibia 12 may be insufficient for mounting tibial tray 12. In these examples, spikes 312A and 312B can be selectively inserted to engage good portions of tibia 12 and/or resected tibial surface 14. In operation of some examples, there can be two spikes, such as spikes 312A and 312B can be secured to any of augment bores 324, 325, 326, and 327 in a pattern that optimizes transmission of forces from the tibial tray (such as tibial tray 104 of FIG. 1) to tibia 12, as desired. In these examples, there can be more bores than spikes, allowing for several configurations of spikes 312A and 312B coupled to tibial tray 304. These examples can allow a physician to select a location of the spikes based upon knee joint kinematics or suitability of tibia 12.

In some examples, such as the example of FIG. 3, two spikes, 312A and 312B, may be required to adequately transfer forces from the tibial tray to tibia 12, via augments 306A and 306B, to prevent rotation of the tibial tray relative to tibia 12. In other examples, more spikes may be required to adequately transfer forces. In one example, two additional spikes may be secured to augment bores 325 and 326 for a total of four spikes (including spikes 312A and 312B). This configuration can further aid the distribution of forces from the tibial tray to tibia 12.

Figure 4:
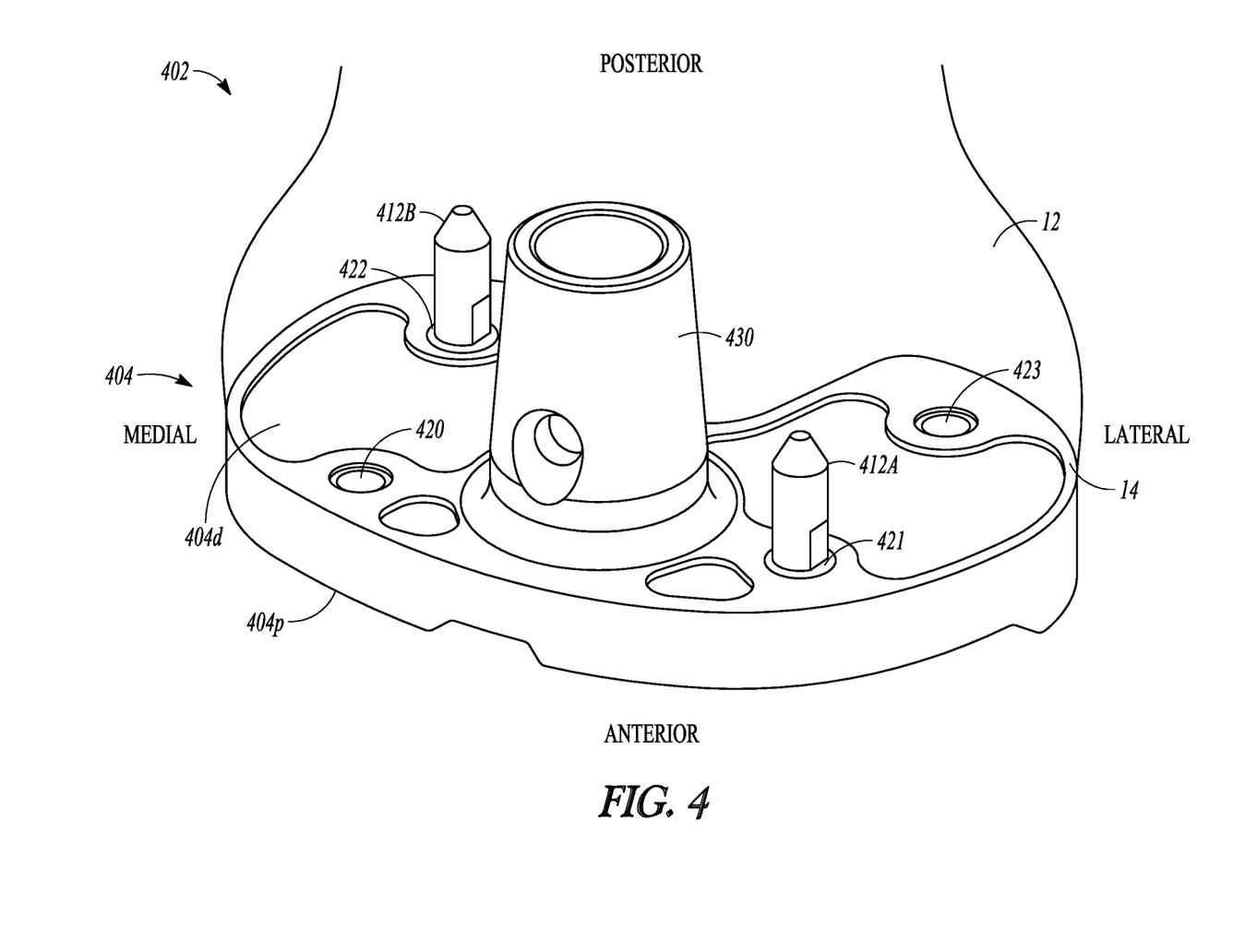
FIG. 4 shows an isometric view of a tibial tray of a tibial replacement system in accordance with an example of the present application.

FIG. 4 shows an isometric view of tibial tray 404 of tibial replacement system 402 in accordance with an example of the present application. Tibial tray 404 can include proximal side 404p, distal side 404d, spikes 412A and 412B, tray bores 420, 421, 422, and 423, and keel stem 430. Also shown in FIG. 4 are tibia 12, resected proximal surface 14, and orientation indications Anterior, Posterior, Medial, and Lateral.

FIG. 4 shows, generally, an example configuration where augments may not be required and spikes 412A and 412B can used to directly secure tibial tray 404 to tibia 12.

Tibial tray 404 can include tray bores 420-423, which can be configured to receive fasteners (not shown) and spikes, such as spikes 412A and 412B as shown in FIG. 4. Tray bores 420-423 can include a threaded portion that can be sized to receive fasteners or additional spikes to secure tibial tray 404 to augments (such as augments 106A and 106B of FIG. 1). The threaded portion of bores 420-423 can also be sized to receive a threaded portion of a spike, such as spikes 412A and 412B in the example of FIG. 4.

Though spike 412B is shown as being coupled to tray bore 422, spike 412B can also be secured to tray bores 420, 421, and 423 in other examples. Similarly, though spike 412A is shown as being coupled to tray bore 421, spike 412A can also be secured to tray bores 420, 422, and 423. In some examples, spikes 412A and 412B can be configured to secure to of any of tray bores 420-423. In these examples, there can be more bores than spikes, allowing for several configurations of spikes 412A and 412B coupled to tibial tray 404. These examples can allow a physician to select a location of the spikes based upon knee joint kinematics or suitability of tibia 12.

In operation of some examples, spikes 412A and 412B can transmit forces from tibia 12 to tibial tray 404 and from tibial tray 404 to tibia 12, helping to prevent rotation of tibial tray 404 relative to tibia 12. This increases the effectiveness and longevity of tibial replacement system 402. In operation of some examples, spikes 412A and 412B can be secured to any of tray bores 420-423 in a pattern that optimizes transmission of forces from tibial tray 404 to tibia 12, as a function of the condition of tibia 12.

In some examples, two spikes, such as spikes 412A and 412B, can be required to adequately transfer forces from tibial tray 404 to tibia 12 to prevent rotation of tibial tray 404 relative to tibia 12. In other examples, more spikes may be required to adequately transfer forces. In one example, two additional spikes may be secured to tray bores 420 and 423 for a total of four spikes (including spikes 412A and 412B). This configuration can further aid the distribution of forces from the tibial tray to tibia 12.

Figure 5A:
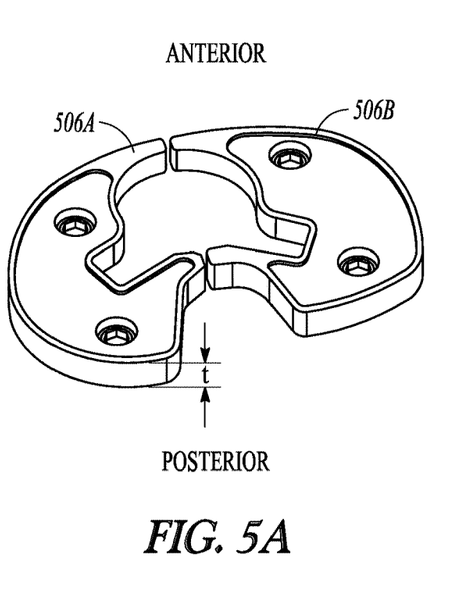
FIGS. 5A-5C show isometric views of augments in accordance with some examples of the present specification.
Figure 5B:
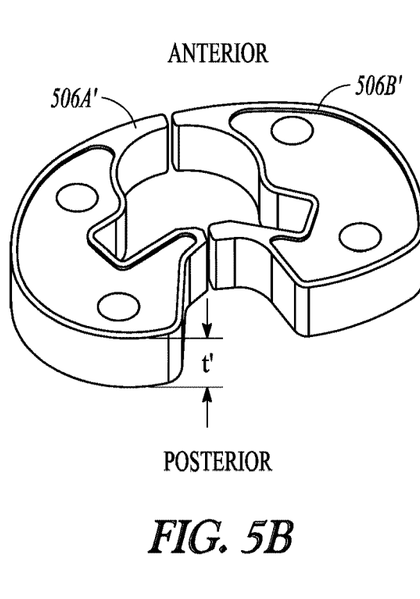
Figure 5C:
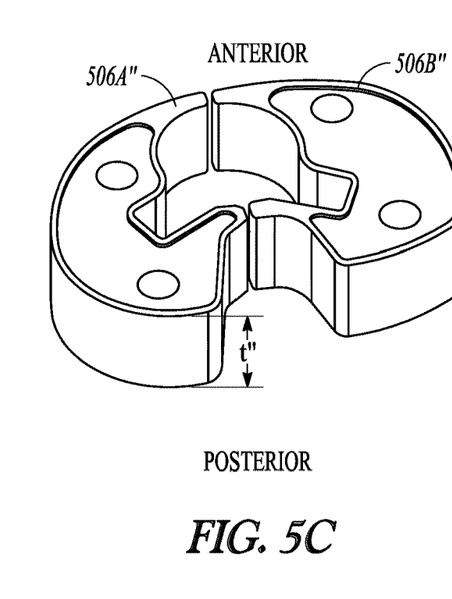

FIGS. 5A-5C show isometric views of examples of augments in accordance with some examples of the present specification. FIGS. 5A-5C show orientation indications Anterior, Posterior, Medial, and Lateral.

FIG. 5A includes augments 506A and 506B and shows augment thickness t. Augment thickness t can be for example, 2 millimeters. In some examples, augment thickness t can be smaller, such as 0.1 millimeters to 1 millimeter. In some other examples augment thickness can be larger, such as 2 to 20 millimeters.

FIG. 5B includes augments 506A' and 506B' and shows augment thickness t'. Augment thickness t' can be for example, 4 millimeters. In some examples, augment thickness t can be smaller, such as 1 millimeter to 4 millimeters. In some other examples augment thickness can be larger, such as 4 to 40 millimeters.

FIG. 5C includes augments 506A" and 506B" and shows augment thickness t". Augment thickness t" can be for example, 8 millimeters. In some examples, augment thickness t can be smaller, such as 2 millimeter to 48 millimeters. In some other examples augment thickness can be larger, such as 8 to 80 millimeters.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A tibial replacement assembly for a knee arthroplasty, the tibial replacement assembly configured to couple to a resected proximal surface of a tibia of a human knee, the tibial replacement assembly comprising:
    a tibial tray comprising a proximal surface and a distal surface opposing the proximal surface wherein the tibial tray includes a first bore and a second bore each having an opening at the distal surface into the tibial tray;
    a first augment having a third bore and a fourth bore therein, the first augment configured to abut the distal surface of the tibial tray and shaped to align the third bore with the first bore and the fourth bore with the second bore;
    a first spike removably secured to and directly connected with the tibial tray and the first augment and extending generally distally away from the distal surface, the first spike configured to extend beneath a resected proximal surface of a tibia, wherein the first spike is removably securable to either the third bore or the fourth bore of the first augment and removably securable to either the first bore or the second bore of the tibial tray, and wherein the first spike secures the first augment to the tibial tray; and
    a first fastener comprising an insert removably securable to and directly connected with the tibial tray and the first augment, wherein the first fastener is removably securable to either the third bore or the fourth bore of the first augment and is removably securable to either the first bore or the second bore of the tibial tray, and wherein the first fastener secures the first augment to the tibial tray.

2. The tibial replacement assembly of claim 1, wherein the first spike is removably received in and securable to the first bore.

3. The tibial replacement assembly of claim 1, further comprising:
    a keel extending generally distally away from the distal surface of the tibial tray; and
    a second augment configured to abut a lateral side of the tibial tray, wherein the first augment is configured to abut a medial side of the tibial tray, and wherein the first and second augments are disposed around the keel.

4. The tibial replacement assembly of claim 1, wherein the tibial tray further comprises:
    a plurality of bores including the first bore, each of the plurality of bores having an opening at the distal surface into the tibial tray.

5. The tibial replacement assembly of claim 4, further comprising:
    a plurality of fasteners including the first fastener; and
    a plurality of a spikes including the first spike, wherein each of the plurality of spikes is configured to secure to any of the plurality of the bores in alternative to one of the plurality of fasteners and each of the plurality of fasteners are configured to secure to any of the plurality of bores in alternative to one of the plurality of spikes.

6. The tibial replacement assembly of claim 5, wherein the plurality of spikes includes a quantity of spikes that is lower than a quantity of the plurality of bores, and wherein the plurality of spikes are each configured to secure into any of the plurality of bores in a pattern as desired.

7. A tibial replacement system for a revision knee arthroplasty, the tibial replacement system couplable to a resected proximal surface of a tibia of a human knee, the tibial replacement system comprising:
    a tibial tray comprising a proximal surface and a distal surface opposing the proximal surface; and
    an augment comprising:
        an augment proximal surface configured to couple to the distal surface of the tibial tray;
        an augment distal surface opposite the augment proximal surface, wherein at least one or both of the distal surface of the tibial tray and the augment distal surface are configured to be disposed on the resected proximal surface of the tibia;
    a first spike removably securable to and directly connected with both of the augment and the tibial tray, the first spike extending generally distally away from the augment distal surface, the first spike configured to extend beneath the resected proximal surface of the tibia; and a first fastener comprising an insert and configured to be removably securable to and directly connected with both of the augment and the tibial tray, wherein the first fastener includes a threaded outer circumference configured to engage corresponding threads of the augment and the tibial tray.

8. The tibial replacement system of claim 7, wherein the tibial tray further comprises:
a first bore having an opening at the distal surface into the tibial tray; and
wherein the augment further comprises a first augment having a second bore therein, wherein the first augment is configured to abut the distal surface of the tibial tray to align the second bore with the first bore.

9. The tibial replacement system of claim 8, further comprising:
a keel extending generally distally away from the distal surface of the tibial tray;
wherein the augment further comprises a second augment configured to abut a lateral side of the tibial tray, wherein the first augment is configured to abut a medial side of the tibial tray, and wherein the first and second augments are disposed around the keel.

10. The tibial replacement system of claim 9, further comprising:
a plurality of fasteners including the first fastener;
a first plurality of bores including the first bore, each having an opening at the distal surface of the tibial tray into the tibial tray; and
a plurality of spikes including the first spike, each spike configured to secure to any of the first plurality of the bores and each fastener is configured to secure to any of the first plurality of bores.

11. The tibial replacement system of claim 10, wherein the plurality of spikes includes a quantity of spikes that is lower than a quantity of the first plurality of bores, and wherein the plurality of spikes are each configured to secure into any of the first plurality of bores in a pattern as desired.

12. The tibial replacement system of claim 11, wherein the augment includes a second plurality of bores, wherein the second plurality of bores are shaped to receive either one of the plurality of spikes or one of the plurality of fasteners, and wherein the plurality of spikes are each configured to secure into any of the first plurality of bores and any of the second plurality of bores and the plurality of fasteners are each configured to secure into any of the first plurality of bores and any of the second plurality of bores.

13. A tibial replacement system for a revision knee arthroplasty, the tibial replacement system couplable to a resected proximal surface of a tibia of a human knee, the tibial replacement system comprising:

a tibial tray comprising a proximal surface and a distal surface opposing the proximal surface; and
an augment comprising:
an augment proximal surface couplable to the distal surface of the tibial tray; and
an augment distal surface opposite the augment proximal surface, wherein the distal surface of the tibial tray and the augment distal surface are both configured to be disposed on a resected proximal surface of a tibia;
a plurality of spikes configured to be removably secured to and directly connected with the augment and the tibial tray, each of the plurality of spikes configured to extend past the augment distal surface to beneath the resected proximal surface of the tibia; and
at least one fastener configured as an insert to be removably secured to and directly connected with both the augment and the tibial tray;
wherein the tibial tray further comprises a first plurality of bores, each of the first plurality of bores having an opening at the distal surface of the tibial tray, wherein the first plurality of bores are shaped to receive either one of the plurality of spikes or one of the at least one fastener, wherein the plurality of spikes includes a quantity of spikes that is lower than a quantity of the first plurality of bores such that the at least one fastener is utilized with at least one of the first plurality of bores, and wherein the plurality of spikes and the at least one fastener are each configured to secure into any of the first plurality of bores in a pattern as desired;
wherein the augment further comprises a second plurality of bores, wherein the second plurality of bores are shaped to receive either one of the plurality of spikes or one of the at least one fastener, and wherein the plurality of spikes and at least one fastener are each configured to secure into any of the first plurality of bores or the second plurality of bores.

14. The tibial replacement system of claim 13, wherein the augment is configured to be positioned to align the second plurality of bores with the first plurality of bores.

15. The tibial replacement system of claim 14, further comprising:
a keel extending generally distally away from the distal surface of the tibial tray;
wherein the augment further comprises a second augment configured to abut a lateral side of the tibial tray and a first augment configured to abut a medial side of the tibial tray, and wherein the first and second augments are disposed around the keel.

* * * * *